(12) United States Patent
Ito et al.

(10) Patent No.: US 7,753,900 B2
(45) Date of Patent: Jul. 13, 2010

(54) DISPOSABLE PULL-ON DIAPER AND PROCESS FOR MAKING THE SAME

(75) Inventors: Kyoko Ito, Kagawa-ken (JP); Kyota Saito, Kagawa-ken (JP); Nariaki Shimoe, Kagawa-ken (JP)

(73) Assignee: Uni-Charm Corporation, Ltd (JP)

( * ) Notice: Subject to any disclaimer, the term of this patent is extended or adjusted under 35 U.S.C. 154(b) by 413 days.

(21) Appl. No.: 10/951,878

(22) Filed: Sep. 29, 2004

(65) Prior Publication Data

US 2005/0070868 A1 Mar. 31, 2005

Related U.S. Application Data

(63) Continuation of application No. PCT/JP03/03647, filed on Mar. 25, 2003.

(30) Foreign Application Priority Data

Mar. 29, 2002 (JP) ............................. 2002-096127

(51) Int. Cl.
*A61F 13/15* (2006.01)
*A61F 13/20* (2006.01)
(52) U.S. Cl. ...................................... 604/394; 604/393
(58) Field of Classification Search ................ 604/389, 604/390, 386, 393, 394, 402
See application file for complete search history.

(56) References Cited

U.S. PATENT DOCUMENTS

| | | | | |
|---|---|---|---|---|
| 5,242,436 A | * | 9/1993 | Weil et al. | 604/385.29 |
| 5,897,546 A | * | 4/1999 | Kido et al. | 604/391 |
| 5,968,030 A | * | 10/1999 | Shimizu et al. | 604/390 |
| 6,641,568 B2 | * | 11/2003 | Ashton et al. | 604/385.01 |
| 6,837,879 B2 | * | 1/2005 | Kuen et al. | 604/385.28 |
| 2003/0034583 A1 | * | 2/2003 | Provost | 264/146 |
| 2004/0116888 A1 | * | 6/2004 | Dorschner | 604/385.22 |

FOREIGN PATENT DOCUMENTS

| | | |
|---|---|---|
| EP | 0 951 885 | 10/1999 |
| EP | 1 121 918 | 8/2001 |
| EP | 1 454 605 | 9/2004 |
| EP | 1 459 721 | 9/2004 |
| EP | 1 498 094 | 1/2005 |
| JP | 05-39531 | 5/1993 |
| JP | 10-099371 | 4/1998 |

\* cited by examiner

*Primary Examiner*—Melanie J Hand
(74) *Attorney, Agent, or Firm*—Lowe Hauptman Ham & Berner, LLP

(57) ABSTRACT

A disposable pull-on diaper includes front and rear waist regions and a pair of tape fasteners secured to an outer surface of the front waist region or the rear waist region. A tape member forming each of the tape fasteners has a distal end portion and a proximal end portion wherein the distal end portion is releasably attached to joining zones along which the front and rear waist regions are joined together.

12 Claims, 3 Drawing Sheets

US 7,753,900 B2

DISPOSABLE PULL-ON DIAPER AND PROCESS FOR MAKING THE SAME

TECHNICAL FIELD OF THE INVENTION

This invention relates to a disposable pull-on diaper for absorption and containment of bodily discharges.

BACKGROUND ART OF THE INVENTION

A disposable pull-on diaper disclosed in Japanese Utility Model Application No. 1993-39531A includes a tape fastener extending in parallel to a periphery of a waist-hole. The tape fastener is attached to one of front and rear waist regions and adapted to be unfolded in a waist-circumferential direction toward the other waist region and to be anchored thereon. The tape fastener is certainly useful to tuck a possible slack of the diaper put on a wearer's body in the waist-circumferential direction.

The tape fastener in the diaper disclosed in the above-cited Application is coated on its inner surface with an adhesive. However, a distal end portion of the tape fastener is not coated with an adhesive and easily gripped with the fingers. The diaper may sometimes encounter a serious problem particularly when the diaper is put on an infant. Specifically, the infant may grip the distal end portion of the tape fastener and pull it from curiosity and result in bringing pollution to the adhesive surface of the tape fastener or twining together of the tape member. Eventually, the tape fastener may fail to function.

SUMMARY

It is an object of this invention to improve the conventional pull-on diaper as disclosed in the above-cited Application so as to eliminate an anxiety that the tape fastener might be unintentionally unfolded.

According to an aspect, a disposable pull-on diaper includes a front waist region, a rear waist region, and a crotch region extending in a longitudinal direction of the diaper between the front and rear waist regions. The diaper further includes transversely opposite lateral edge portions of the front and rear waist regions being permanently joined together in joining zones so as to form a waist-hole and a pair of leg-holes; a pair of tape fasteners attached to an outer surface of one of the front and rear waist regions; and each of the tape fasteners being elongated in a transverse direction of the diaper.

Each of the tape fasteners has opposite proximal and distal end portions, the proximal end portion being directly secured to the one of the front and rear waist regions while the distal end portion overlaying the respective lateral edge portion of the one of the front and rear waist regions and being directly releasably attached to the one of the front and rear waist regions in at least one of the joining zones so as to serve as a finger-grip, and an intermediate portion formed between and connecting the proximal end portion and the distal end portion and adapted to be releasably anchored on the other of the front and rear waist regions.

The joining zones includes a plurality of depressions in which the respective lateral edge portions of the front and rear waist regions are compressed and permanently joined together. The distal end portion of each of the tape fasteners and the respective lateral edge portions of the front and rear waist regions are all compressed together in at least one of the depressions, and wherein, in the at least one depression, the distal end portion is also directly releasably welded to the respective lateral edge portion of the one of the front and rear waist regions.

According to another aspect, a disposable pull-on diaper includes a front waist region, a rear waist region, and a crotch region extending in a longitudinal direction of the diaper between the front and rear waist regions. The diaper further includes transversely opposite lateral edge portions of the front and rear waist regions being permanently joined together in joining zones so as to form a waist-hole and a pair of leg-holes; a pair of tape fasteners attached to an outer surface of one of the front and rear waist regions; and each of the tape fasteners being elongated in a transverse direction of the diaper.

Each of the tape fasteners has opposite proximal and distal end portions, the proximal end portion being directly secured to the one of the front and rear waist regions while the distal end portion overlaying the respective lateral edge portion of the one of the front and rear waist regions and being directly releasably attached to the one of the front and rear waist regions in at least one of the joining zones so as to serve as a finger-grip, and an intermediate portion formed between and connecting the proximal end portion and the distal end portion and adapted to be releasably anchored on the other of the front and rear waist regions.

The joining zones include a plurality of depressions in which the respective lateral edge portions of the front and rear waist regions are compressed together.

The distal end portion of each of the tape fasteners and the respective lateral edge portions of the front and rear waist regions are all compressed together in at least one of the depressions, and wherein, in the at least one depression, the distal end portion is also directly, releasably and mechanically engaged with a material forming the respective lateral edge portion of the one of the front and rear waist regions.

DETAILED DESCRIPTION

Details of the disposable pull-on diaper according to this invention and the process for making this will be more fully understood from the description given hereunder in reference to the accompanying drawings.

Figure 1:
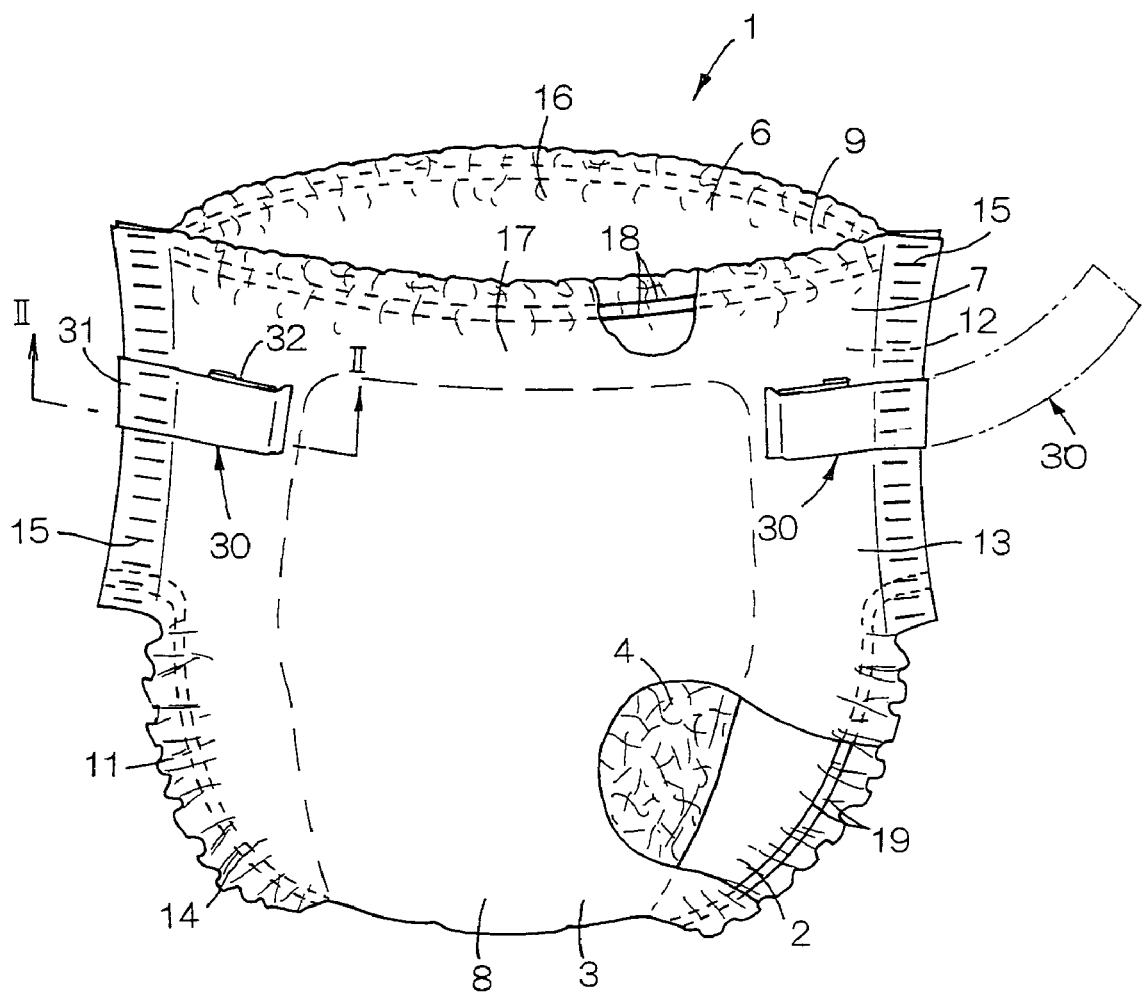
FIG. 1 is a partially cutaway perspective view showing a pull-on diaper constructed in accordance with this invention.

FIG. 1 shows a partially cutaway disposable pull-on diaper as viewed from the rear side. The diaper 1 comprises a liquid-pervious topsheet 2, a liquid-impervious backsheet 3 and a liquid-absorbent core 4 disposed between these sheets 2, 3. From the viewpoint of its configuration, the diaper 1 is composed of a front waist region 6, a rear waist region 7 and a crotch region 8 so as to define a waist-hole 9 and a pair of leg-holes 11. As viewed in FIG. 1, the rear waist region 7 lies on near side. The top- and backsheets 2, 3 extend outward beyond a peripheral edge of the core 4 and are overlaid and intermittently joined together along the extensions thereof using an adhesive or a heat-sealing technique so as to form transversely opposite lateral edge portions 12, 13 of the front and rear waist regions 6, 7, longitudinal end zones 16, 17 of these front and rear waist regions 6, 7, respectively, and transversely opposite lateral edge portions 14, 14 of the crotch region 8, i.e., zones extending in a leg-circumferential direction. The front and rear waist regions 6, 7 are overlaid together in the vicinity of the lateral edge portions 12, 13 and joined together rather firmly in joining zones 15 comprising a plurality of short lines arranged intermittently in a vertical direction along marginal side edges of the respective lateral edge portions 12, 13. Along the longitudinal end zones 16, 17 of the front and rear waist regions and along the lateral edge portions 14, 14 extending in the leg-circumferential direction, waist elastic members 18 and leg elastic members 19 are secured in a stretched state to an inner surface of at least one of the top- and backsheets 2, 3, respectively. It should be noted that the expression used herein "rather firmly" means that the lateral edge portions 12, 13 well resist against mutual separation thereof so far as the diaper 1 is under the normal condition of use but a positive intention to separate these lateral edge portions 12, 13 one from another, for example, forceful pulling them one from another in the waist-circumferential direction causes these lateral edge portions 12, 13 to be separated one from another. It should be also understood that such separation includes a case in which the lateral edge portions 12, 13 are peeled off one from another in the joining zones 15 and a case in which the lateral edge portions 12, 13 are separated one from another as a result of breakage of the topsheet 2 or the backsheet 3 in these lateral edge portions 12, 13.

A pair of tape fasteners 30 are attached to the lateral edge portions 13, 13 of the rear waist region 7, respectively. Each of the tape fasteners 30 is formed of tape material extending on in a transverse direction of the diaper 1 and folded on the rear waist region 7. The tape fastener 30 has a fixed end portion 32 secured to the backsheet 3 in the associated lateral edge portion 13 and a free end portion 31 serving as a finger grip releasably attached to the backsheet 3 in the associated lateral edge portion 13 so as to overlay the associated joining zone 15. The free end portion 31 may be released from the backsheet 3 and then pulled outward in the transverse direction of the diaper 1 to unfold the tape fastener 30 as indicated by imaginary lines.

Figure 2:
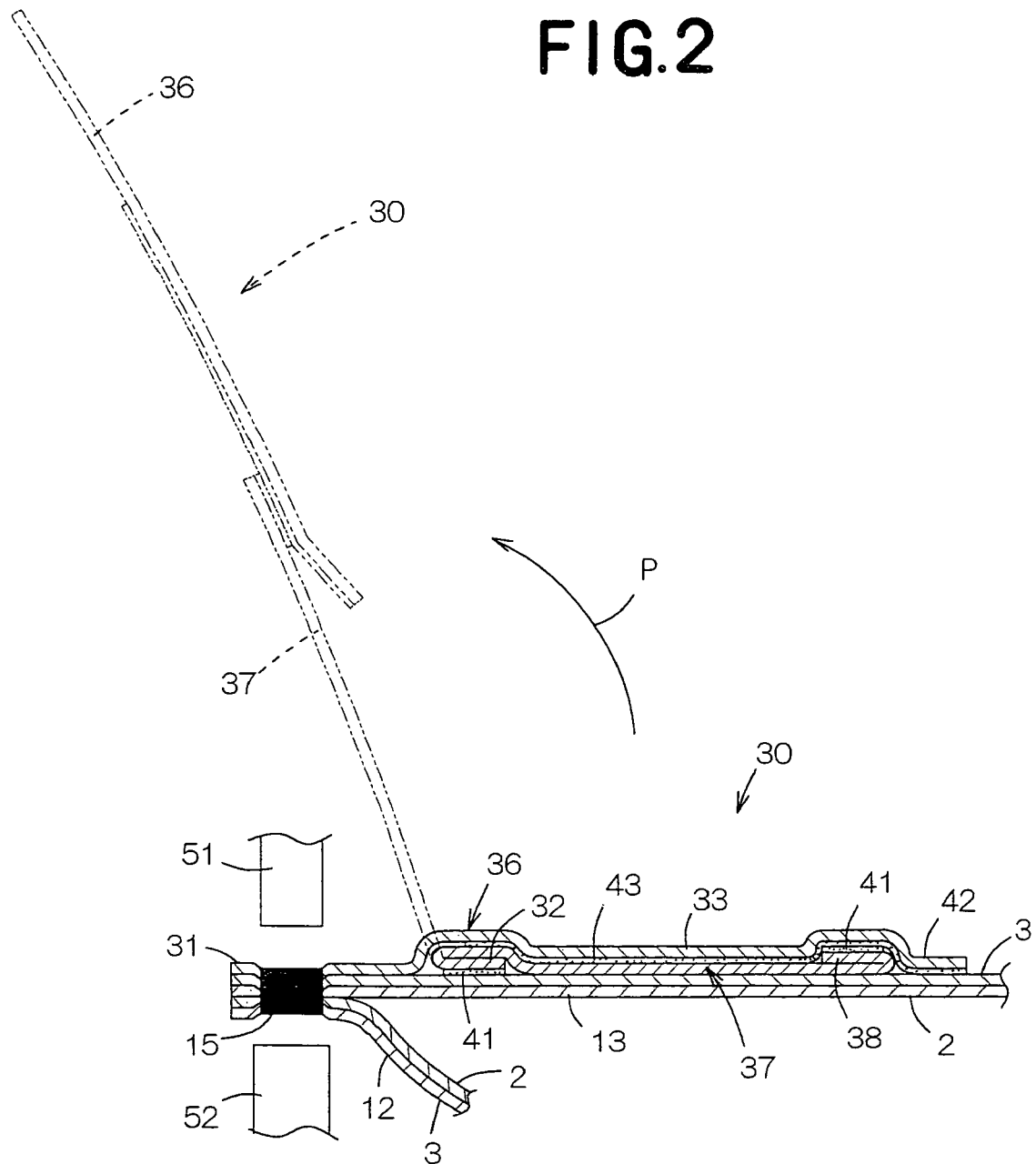
FIG. 2 is a sectional view taken along a line II-II in FIG. 1 showing a hone and an anvil also.

FIG. 2 is a sectional view taken along a line II-II in FIG. 1, showing also a hone 51 and an anvil 52 for supersonic embossing used to form the joining zones 15. The tape fastener 30 comprises a first tape section 36 extending rather linearly to define an upper layer as viewed in FIG. 2 and a second tape section 37 folded substantially in Z-shape under the first tape section 36. The second tape section 37 has an inner end portion 38 folded upward and secured to an under surface of the first tape section 36 by means of an adhesive 41 and an outer end portion opposite to the inner end portion 38 i.e., the proximal end portion 32 secured to the backsheet 3 by means of the adhesive 41. The first tape section 36 is coated on its substantially entire under surface except for its outer end portion, i.e., the distal end portion 31 with a self-adhesive 43. The first tape section 36 has an inner end portion 42 extending inward of the diaper 1 beyond the inner end portion 38 of the second tape section 37 and releasably attached to the backsheet 3 by means of the self-adhesive 43. The first tape section 36 has an intermediate portion 33 defined between the distal end portion 31 and the inner end portion 42 and releasably attached to an upper surface of the second tape section 37 by means of the self-adhesive 43. The distal end portion 31 is releasably integrated with the joining zone 15 in the associated lateral edge portion 13. The expression used herein "releasably" means that, when the fastener 30 is actually used, the distal end portion 31 may be gripped with the fingers and pulled in a direction indicated by an arrow P to separate the distal end portion 31 easily from the associated joining zone 15 and to extend the tape fastener 30 outward beyond the associated lateral edge portion 13.

In such diaper 1, stock material for the topsheet 2 is selected from the group including a thermoplastic synthetic resin film, a nonwoven fabric made of thermoplastic synthetic resin fibers and a composite nonwoven fabric made from a mixture of thermoplastic synthetic resin fibers and natural or chemical fibers. A stock material for the backsheet 3 is selected from the group including a thermoplastic synthetic resin film and a laminated sheet of such film and a nonwoven fabric which is made of thermoplastic synthetic fibers. The film for the top- and backsheets 2, 3 may be, for example, of a polyethylene resin. The fiber for the top- and backsheets 2, 3 may be resin such as polyethylene, polypropylene, nylon or polyester. It is also possible to use conjugated fibers of side-by-side type or sheath-and-core type of these fibers as the fiber for the top- and backsheets 2, 3. To connect the front and rear waist regions 6, 7 to each other along the lateral edge portions 12, 13 thereof, the top- and backsheets 2, 3 overlaid along the lateral edge portions 12, 13 thereof may be subjected to a process of embossing, heat-embossing or supersonic embossing to form the joining zones 15. In such process, the top- and backsheets 2, 3 are locally pressed so that the film and/or the fiber constituting these sheets 2, 3 may be mechanically entangled together at the pressed locations and thereby inseparably integrated together. Particularly the process of supersonic embossing results not only in such mechanical entangling of the film and/or the fiber of thermoplastic resin but also in melting and integration of one or both of the film and/or the fiber. FIG. 2 illustrates a hone 51 and an anvil 52 for the process of supersonic embossing are placed above and below the lateral edge portions 12, 13 placed upon each other. These lateral edge portions 12, 13 may be squeezed between the hone 51 and the anvil 52 under a supersonic effect to form the joining zones 15.

Regarding the tape fastener 30, a film of a thermoplastic synthetic resin such as polyethylene, polypropylene, nylon or polyester is preferably used to form at least the free end portion 31 of the first tape section 36, more preferably to form the first tape section 36 as a whole. The film or the fiber forming the distal end portion 31 preferably has a softening point or a melting point higher than that of the film or the fiber forming the backsheet 3 which the former is opposed in the joining zone 15. A stock material for the second tape section 37 may be selected from the group including a film of a thermoplastic synthetic resin, a nonwoven fabric of thermoplastic synthetic resin fibers and an elastically stretchable elastomer of a thermoplastic synthetic resin. To attach the tape fastener 30 formed as has been described above to the diaper 1, the tape fastener 30 is placed upon the lateral edge portion 12 or 13 of the diaper 1 with the distal end portion 31 defining the outermost portion of the fastener 30 and then subjected to the process of embossing, for example, under the heat or supersonic effect to form the joining zone 15. Thereupon, surfaces of the topsheet 2 opposed to each other or the topsheet 2 and the backsheet 3 are inseparably welded together while the backsheet 3 having a relatively low softening or melting point and the distal end portion 31 of the tape fastener 30 having a relatively high softening or melting point are releasably integrated together at an attaching strength as low as that of so-called temporary attaching. When the backsheet 3 and the free end portion 31 respectively have a softening or melting point approximate to each other, a thickness of the distal end portion 31 may be dimensioned to be larger than a thickness of the backsheet 3, for example, at least trebled with respect to that of the backsheet 3 to ensure that the free end portion 31 can be easily separated from the backsheet 3 without any significant damage thereof even after having been subjected to the process of a simple embossing or a heat-embossing.

Figure 3:
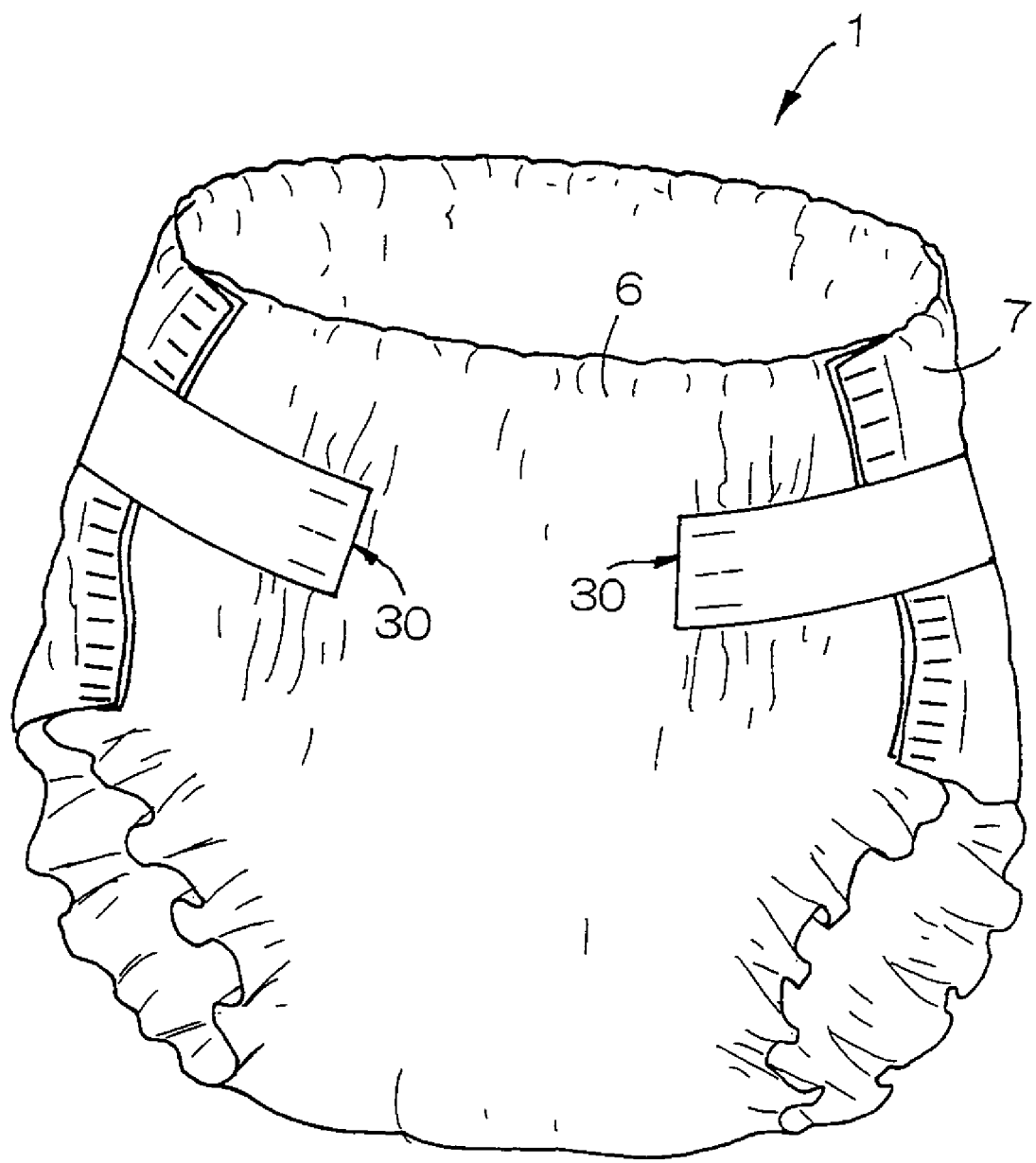
FIG. 3 is a perspective view of the diaper illustrating a manner in which the tape fasteners are used.

FIG. 3 illustrates a manner in which the tape fastener 30 is actually used. Having been released from the associated joining zone 15, the tape fastener 30 may be unfolded toward the front waist region 6 and anchored on an appropriate zone of the front waist region 6 by means of the self-adhesive 43 so as to tuck a baggy dimension in the waist-circumferential direction. Though not illustrated, the tape fastener 30 can be used also to retain the used diaper 1 in a rolled up state for disposal.

As will be apparent from the foregoing description, the tape fastener 30 has its free end portion 31 temporarily attached to the associated lateral edge portion 12 or 13 of the diaper 1 so that the free end portion 31 may be easily separated therefrom to use the tape fastener 30. However, it is not likely that the tape fastener 30 might be unintentionally unfolded even if the diaper wearing infant touches the fastener 30 in curiosity. The self-adhesive 43 may be replaced by a hook member or a loop member constituting so-called mechanical fastener commonly known, for example, by the trade name of Magic Tape. When the self-adhesive 43 is replaced by the hook member of these paired members, the waist region 6 or 7 on which this hook member should be attached is provided with a landing zone defined by the loop member. It should be understood that, if the backsheet 3 is formed by a nonwoven fabric, this nonwoven fabric itself can be used as the landing zone. This invention is not limited to the construction in which the front and rear waist regions 6, 7 are overlaid along the lateral edge portions 12, 13 thereof as seen in the embodiment shown in FIG. 1. For example, this invention can be implemented in the other various manners, for example, these lateral edge portions 12, 13 may extend and alternately overlap one another in the waist-circumferential direction of the diaper 1. While FIG. 2 illustrates the second tape section 37 folded substantially in a Z-shape as viewed in its cross-section, the manner in which the second tape section 37 is folded is not specified. For example, the length as well as the number of layers presented by the folded second tape section 37 may be selectively varied.

In the disposable pull-on diaper according to this invention, the tape fasteners secured to the waist region respectively have the distal end portions temporarily attached to the waist region but there is no anxiety that these distal end portions might be unintentionally separated from the waist region even if the diaper wearing infant touches them in curiosity.

What is claimed is:

1. A disposable pull-on diaper, comprising:
a front waist region, a rear waist region, and a crotch region extending in a longitudinal direction of said diaper between said front and rear waist regions;
transversely opposite lateral edge portions of said front and rear waist regions being permanently joined together in joining zones so as to form a waist-hole and a pair of leg-holes;
a pair of tape fasteners attached to an outer surface of one of said front and rear waist regions; and
each of said tape fasteners being elongated in a transverse direction of said diaper and having:
opposite proximal and distal end portions, said proximal end portion being directly secured to said one of said front and rear waist regions while said distal end portion overlaying the respective lateral edge portion of said one of said front and rear waist regions and being directly releasably attached to said one of said front and rear waist regions in at least one of the joining zones so as to serve as a finger-grip, and
an intermediate portion formed between and connecting said proximal end portion and said distal end portion and adapted to be releasably anchored on the other of said front and rear waist regions;
wherein said joining zones comprise a plurality of depressions in which the respective lateral edge portions of said front and rear waist regions are compressed and permanently joined together,
wherein the distal end portion of each of said tape fasteners and the respective lateral edge portions of said front and rear waist regions are all compressed together in at least one of said depressions, and wherein, in said at least one depression, said distal end portion is also directly releasably welded to the respective lateral edge portion of said one of said front and rear waist regions.

2. A disposable pull-on diaper, comprising:
a front waist region, a rear waist region, and a crotch region extending in a longitudinal direction of said diaper between said front and rear waist regions;
transversely opposite lateral edge portions of said front and rear waist regions being permanently joined together in joining zones so as to form a waist-hole and a pair of leg-holes;
a pair of tape fasteners attached to an outer surface of one of said front and rear waist regions; and
each of said tape fasteners being elongated in a transverse direction of said diaper and having:
opposite proximal and distal end portions, said proximal end portion being directly secured to said one of said front and rear waist regions while said distal end portion overlaying the respective lateral edge portion of said one of said front and rear waist regions and being directly releasably attached to said one of said front and rear waist regions in at least one of the joining zones so as to serve as a finger-grip, and
an intermediate portion formed between and connecting said proximal end portion and said distal end portion and adapted to be releasably anchored on the other of said front and rear waist regions;
wherein said joining zones comprise a plurality of depressions in which the respective lateral edge portions of said front and rear waist regions are compressed together,
wherein the distal end portion of each of said tape fasteners and the respective lateral edge portions of said front and rear waist regions are all compressed together in at least one of said depressions, and wherein, in said at least one depression, the distal end portion is also directly, releasably and mechanically engaged with a material forming the respective lateral edge portion of said one of said front and rear waist regions.

3. The diaper according to claim 1, wherein, in each of said tape fasteners, the proximal end portion directly secured to the outer surface of said one of said front and rear waist regions is spaced inwardly in the transverse direction from the respective distal end portion, which is directly releasably attached to said one of said front and rear waist regions in said at least one depression.

4. The diaper according to claim 1, wherein, in each of said tape fasteners, the proximal end portion is directly secured by adhesive to the outer surface of said one of said front and rear waist regions and is spaced inwardly in the transverse direction from the respective distal end portion, which is directly releasably attached to said one of said front and rear waist regions in said at least one of the depressions.

5. The diaper according to claim 2, wherein
in each of said tape fasteners, the proximal end portion is directly secured by adhesive to the outer surface of said one of said front and rear waist regions and is spaced inwardly in the transverse direction from the respective distal end portion, which is directly releasably attached to said one of said front and rear waist regions in said at least one of the depressions, and in said at least one of said depressions, thermoplastic synthetic fibers contained in the respective lateral edge portions of said front and rear waist regions are inseparably mechanically entangled together and releasably joined to the distal end portion of the respective one of said tape fasteners.

6. The diaper according to claim 4, wherein, in said at least one of said depressions, thermoplastic synthetic resins contained in the respective lateral edge portions of said front and rear waist regions are inseparably welded together and are releasably welded to the distal end portion of the respective one of said tape fasteners.

7. The diaper according to claim 6, wherein the thermoplastic synthetic resins contained in the respective lateral edge portions of said front and rear waist regions have a softening point or a melting point lower than that of a thermoplastic synthetic resin contained in the distal end portion of the respective tape fastener, thereby allowing the thermoplastic synthetic resins in the respective lateral edge portions in said at least one of said depressions to be inseparably welded together and releasably welded to the thermoplastic synthetic resin in the distal end portion of the respective tape fastener.

8. The diaper according to claim 6, wherein the thermoplastic synthetic resins contained in the respective lateral edge portions of said front and rear waist regions have a softening point or a melting point approximate to that of a thermoplastic synthetic material contained in the distal end portion of the respective tape fastener; and the thermoplastic synthetic resins contained in the respective lateral edge portions have a thickness less than that of the thermoplastic synthetic material contained in the distal end portion of the respective tape fastener, thereby allowing the thermoplastic synthetic resins in the respective lateral edge portions in said at least one of said depressions to be inseparably welded together and releasably welded to the thermoplastic synthetic material in the distal end portion of the respective tape fastener.

9. The diaper according to claim 8, wherein the thickness of said thermoplastic synthetic material contained in the distal end of each said tape fastener is at least three times greater than the thickness of said thermoplastic synthetic resins contained in the respective lateral edge portions of said front and rear waist regions.

10. The diaper according to claim 6, wherein said at least one of said depressions includes melted and solidified said thermoplastic synthetic resins contained in the respective lateral edge portions of said front and rear waist regions; and a thermoplastic synthetic resin contained in the distal end portion of the respective tape fastener and releasably heat-bonded to said melted and solidified thermoplastic synthetic resins in the respective lateral edge portions.

11. The diaper according to claim 1, wherein each said fastener is in a folded state and comprises a first tape section, and a second tape section which is sandwiched, in said folded state of the fastener, between the first tape section and the outer surface of said one of said front and rear waist regions;

wherein the first tape section comprises the respective distal end portion which is, in said folded state of the fastener, directly releasably welded to the respective lateral edge portion of said one of said front and rear waist regions in said at least one depression, and a first inner end portion which is, in said folded state of the fastener, inwardly spaced in the transverse direction from said distal end portion; the second tape section comprises the respective proximal end portion directly secured to the outer surface of said one of said front and rear waist regions at a location that is, in said folded state of the fastener, inwardly spaced in the transverse direction from said distal end portion, and a second inner end portion which is bonded to the first inner end portion and, in said folded state of the fastener, inwardly spaced in the transverse direction from said proximal end portion.

12. The diaper according to claim 11, wherein each said fastener further comprises a fastening element adapted to be releasably anchored on the other of said front and rear waist regions;

wherein said fastening element is disposed on a underside of said first tape section and is, in said folded state of the fastener, located between the first and second tape sections to releasably attach the first tape section to the underlying second tape section.

\* \* \* \* \*